United States Patent [19]
Verdicchio et al.

[11] Patent Number: 6,156,323
[45] Date of Patent: *Dec. 5, 2000

[54] TRICOT-LIKE POUCH FOR THE DELIVERY OF TOPICAL DRUGS AND COSMETICS

[75] Inventors: Robert J. Verdicchio, Succasunna; Morris Yang, Princeton Junction; Samuel E. Carasso, Milltown; Kurt Stenn, Princeton, all of N.J.

[73] Assignee: Johnson & Johnson Consumer Companies, Inc., Skillman, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/495,727

[22] Filed: Jun. 8, 1995

[51] Int. Cl.⁷ ....................................................... A61F 13/02
[52] U.S. Cl. .................... 424/401; 424/402; 424/443; 424/444; 424/445; 424/449; 428/516
[58] Field of Search ............................ 428/516; 424/401, 424/402, 448, 443, 444, 449, 445

[56] References Cited

U.S. PATENT DOCUMENTS

| | | |
|---|---|---|
| 324,276 | 8/1885 | Schribner . |
| 3,632,269 | 1/1972 | Dovink et al. ............................ 425/362 |
| 3,871,376 | 3/1975 | Kozak ..................................... 128/275.1 |
| 3,929,135 | 12/1975 | Thompson ................................... 128/287 |
| 4,341,207 | 7/1982 | Steer et al. ................................ 128/155 |
| 4,381,326 | 4/1983 | Kelly .......................................... 428/134 |
| 4,560,372 | 12/1985 | Pieniak ....................................... 604/369 |
| 4,596,738 | 6/1986 | Metcalfe et al. ........................ 428/308.4 |
| 4,614,679 | 9/1986 | Farrington, Jr. et al. ................ 428/138 |
| 4,690,679 | 9/1987 | Mattingly, III et al. . |
| 4,810,499 | 3/1989 | Nuwayser ................................. 424/448 |
| 4,839,216 | 6/1989 | Curro et al. .............................. 428/134 |
| 4,846,164 | 7/1989 | Martz ........................................ 128/155 |
| 4,909,244 | 3/1990 | Quarfoot et al. ......................... 128/156 |
| 5,455,110 | 10/1995 | Connor ...................................... 428/286 |
| 5,861,058 | 1/1999 | Fuesser et al. ............................. 117/90 |

FOREIGN PATENT DOCUMENTS 0304617  3/1989  European Pat. Off. .

*Primary Examiner*—Jose' G. Dees
*Assistant Examiner*—Kathryne E. Shelborne

[57] ABSTRACT

This invention relates to pouch or pledget delivery system having an apertured film or fabric covering which assists in evenly and safely distributing topical medicaments.

16 Claims, 3 Drawing Sheets

(1 of 3 Drawing Sheet(s) Filed in Color)

TRICOT-LIKE POUCH FOR THE DELIVERY OF TOPICAL DRUGS AND COSMETICS

FIELD OF INVENTION

This invention relates to a safe, economical delivery system for cosmetics, toiletries, and over-the-counter) drugs. More particularly, it relates to a pouch-like delivery system having a tricot-like film covering which assists in evenly and safely distributing topical medicaments.

PRIOR ART

Development of a safe economical delivery system for cosmetics, toiletries, and OTC (over the counter) drugs has been a long-sought goal. The advantages of developing such a system include convenience, as well as good aesthetics and safety. For example, baby and body powders produce dust from conventional containers presenting an inhalation problem. Ointments used for infant diaper rash treatment are messy and difficult to spread when dispensed from a tube or jar type package. Many topically- applied OTC drugs are sensitive to ultraviolet light and require elaborate and expensive packaging. In addition, dosage regulation for the latter is costly, particularly when over-use is a safety concern.

Nonwoven fabrics have been used for a wide variety of applications for at least fifty years. Nonwoven fabrics are textile-like materials produced directly from a web of fibers so as to eliminate the many time consuming steps involved in converting staple length fibers into woven or knitted goods. Nonwoven fabrics are inherently porous structures, i.e. they contain openings or pores allowing for the passage of fluids such as air and water or aqueous solutions. In addition, nonwoven fabrics may be tailored so as to have good softness, drapability, and tactile impression. Due to their desirable characteristics, nonwovens have been employed as facing materials for absorbent products such as disposable diapers, washcloths and the like. However, they have been limited to the above as a result of insufficient durability, relatively high cost and versatility of design ingredient loading and product payoff. These disadvantages do not lend their application to the formation of a suitable delivery system for dispensing personal care/drug products to hair and skin.

Apertured plastic films have been known to be used as facing materials heretofore as well. For example, an apertured plastic film may be produced by placing a heated thermoplastic sheet material on a patterned perforated surface and applying a vacuum thereto. The vacuum pulls the softened sheet material through the perforations, thereby causing the film to rupture and form apertures.

U.S. Pat. No. 3,929,135 (Thompson et al.) describes perforated topsheet materials for absorbent devices such as sanitary napkins, incontinent pads, bandages and the like. These topsheet materials are constructed from liquid impervious materials such as low density polyethylene and comprise a plurality of tapered capillaries each of which has a base opening in the plane of the top sheet and an apex opening which is remote from the plane of the top sheet.

U.S. Pat. No. 4,324,276 (Mullane) describes an apertured formed film having a caliper of less than about 0.030 inch (0.075 cm), an open area of a least 35% and a plurality of apertures at least 75% of which have an equivalent hydraulic diameter (EHD) of at least 0.025 inch (0.064 cm), which is useful as a topsheet for disposable absorbent products of the type mentioned above.

U.S. Pat. No. 4,839,216 (Curro et al.) describes a debossed and perforated plastic material produced by providing a starting film on a perforated forming surface and applying an unconstrained liquid stream to the upper surface of the starting film.

European Patent Application 0 304 617 (Kao Corporation) describes a covering sheet for a sanitary article. The covering sheet comprises an opaque, hydrophobic film having land portions and recesses, said recesses being formed to have a bottom portion and side walls. The side walls have a slanting part which is provided with an opening such that the slanting part is not covered by the land portion.

U.S. Pat. No. 4,690,679 describes an apertured film comprising a first layer of a first polymeric film and a second layer of a second polymeric film. This patent states that apertured films wherein the apertures have average equivalent circular diameters ranging from about 0.010 inches (0.0254 cm) to about 0.030 inches (0.0762 cm) are useful as covering materials for absorbent products.

Other patents relating to apertured films and methods and apparatus for making the same include U.S. Pat. No. 3,632,269 to Doviak et al. and U.S. Pat. No. 4,381,326 to Kelly.

The fabric as previously defined is a tricot-like fabric made from LLDPE, LDPE, PP, EVA, EMA (ethylene methyl acrylate) and coextrusion or blend of above-identified polymers, blown or cast film with 0.5 to 3 mil thickness.

There have been many attempts to design a pouch to facilitate delivery of drugs and other compositions for this use. For example, U.S. Pat. No. 5,368,581 (Smith et.al.) describes a method of applying two or more drug agents to skin from a single dispensing applicator system having a plurality of applicator pads. It consists of a C-fold or face-to-face shield which must be separated by hand by tearing the facings (C-folds). The liquids are impregnated onto the pads prior to tearing and mixed in-situ on the skin by rubbing. U.S. Pat. No. 3,647,305 (Baket et.al.) describes a similar applicator with C-fold or face-to-face sealing which is convertible to a multi-finger pad with drug agents. The drug agents are applied from either a saturated porous nonwoven pad or open-celled foam. The basic pad is a non-sealable latex film in which the non-sealable latex film is coated with a heat sealable latex film. The basic pad must be opened or inverted prior to use in or to apply the contents.

Similarly, U.S. Pat. No. 2,621,784 (Boytham) describes a medicant applicator package consisting of the following: a single sheet of impervious fusible material with face-to-face sealing of the absorbent medicant containing pads in a manner to form a G-fold. It also contains a compartment for placement of hand or fingers on the back. The impervious material must be removed prior to using a string which surrounds the entire package.

All of the above suffer from one or more of deleterious drawbacks. For example, the package of Smith et al. has many applicator pads which are C-folded (face-to-face). They must be torn to activate the product, which is inconvenient and can lead to product spillage and entrapment of the drug agents. In addition, the active agents must be mixed in-situ on skin which can produce an uneven mixture of the components. The package described by Backet et al. also suffers from product entrapment or in the case of saturation, a lack of control vis-a-vis spillage. In addition, the absorbent pad must be inverted prior to application, which is cumbersome. Boytham's G-folded product is activated using a string and is therefore clumsy and can lead to product spillage and lack of control. The Boytham product, as well as the Backet et al. and the Smith et al. products may cause entrapment of the active ingredient, i.e., the inability to expel the full dosage of active ingredient from the pad. In addition, all of the above products and, in particular, the applicator pad require that the active ingredient be impregnated into absorbent materials such as non-woven or sponge.

Tricot knit fabrics are durable, soft and drapable. The tricot fabric structure provides high quality perception, good aesthetics, and luxurious appeal. No apertured film in the market today has tricot appearance and feel.

Based on the foregoing, it is an object of this invention to provide a tricot-like fabric or film pouch for delivery of topical personal care and drug products.

It is further an object of this invention to provide a soft, cost effective and convenient delivery system for the above for use on hair and skin.

Another object of this invention is to provide a delivery system for medicaments which is simple to use, expels a large percentage of medicament upon finger pressure and yet is neat, protecting the skin of the individual who is making the application of medicament.

It is still further an object of this invention to provide safety and product/ingredient integrity for consumer use and protection.

BRIEF DESCRIPTION OF THE DRAWINGS

The file of this patent contains at least one drawing executed in color. Copies of this patent with color drawings are provided to the Patent and Trademark Office with payment of the necessary fee.

SUMMARY OF THE INVENTION

Figure 1:
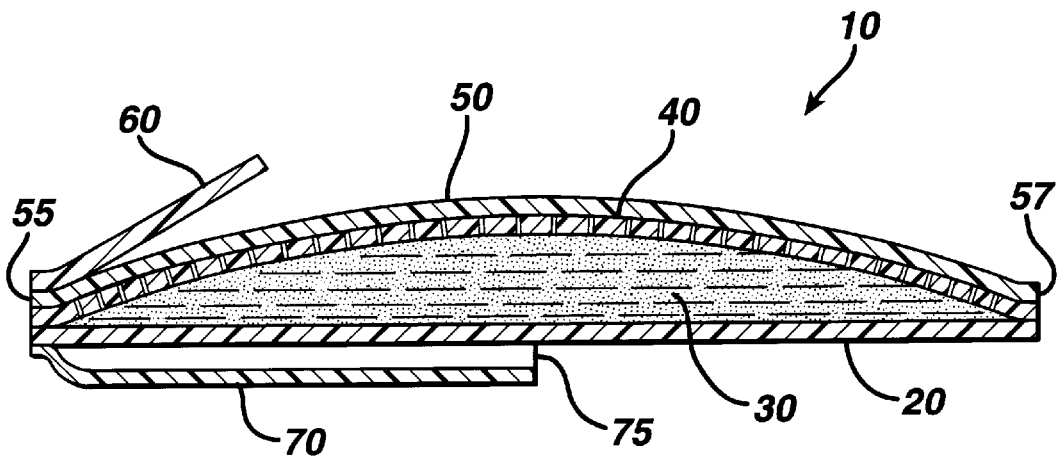
FIG. 1 depicts a cross-section of one embodiment of a delivery system pouch according to this invention.

This invention relates to an improved package system for delivery of drugs, cosmetics and toiletries which are intended for topical use. These can be used on humans, animals and plants. In addition, any products which can be dispensed using such a package system can be incorporated in the improved package system of this invention so as to deliver a composition to an inanimate object or surface. For example, the improved package system of this invention may be used to deliver shoe polish to a shoe surface, keeping the hands clean while eprforming this task.

The products of this invention relate to a delivery pouch having a backing, a delivery facing and a coating of active material therebetween. The delivery pouch preferably is made of novel apertured films which comprise a plurality of micro-holes defined by a network of fiber-like elements or microstrips of drawn plastic as described in copending patent application U.S. Ser. No. 08/307,973. This film fabric, which is tricot-like, is applicable to personal care and drug products as unique delivery systems as a result of the inherent properties as defined herein. However, other films or fabrics having similar attributes may be used as well. This represents numerous advantages to the consumer as will become apparent hereinafter.

The products of this invention preferably contain at least an impermeable backing, a coating of medicament and, overlying said coating and sealed to said impermeable backing. More preferably they contain the following elements:

(a) a peel tab
(b) a detachable cover
(c) a delivery facing
(d) a coating of active ingredient in paste or gel form
(e) an impermeable backing
(f) a finger pocket.

All these components are sealed using radiant energy, such as heat, radiation or ultrasound.

The products of this invention provide many benefits over the systems described heretofore. For example, the bonding between the detachable cover and the delivery facing is weaker than that between the delivery facing and the impervious backing,thereby permitting the detachable cover to be peeled back without loosening the delivery facing from the backing. This provides considerably improved control of the pouch using the finger pocket. The detachable cover is preferably a polymer film, preferably a polyalkylene film such as polypropylene, polyethylene, polyester or paraffin wax-coated paper. The peel tab is preferably a polypropylene and ethylene-vinyl acetate coextruded film or paper/film with adhesive coating. In this way, the ethylene-vinyl acetate side of the coextruded film can be sealed to the polypropylene detachable cover material and create a strong seal which can readily assist in removing the detachable cover from the delivery facing without affecting the ability of the delivery facing to be adhered to the impervious backing.

The delivery facing is preferably a soft, two-dimensional film with a three-dimensional structure having a fabric-like feel. In other words, the film itself is two-dimensional, but it is made in such a way that the final product has three dimensions, i.e. it has undulations. Preferably, the film does not have interstitial spaces, which would permit the active ingredient to be entrapped therein. This provides the products of this invention with enhanced containment and release properties. The film or fabric useful in the products of this invention preferably has a three dimensional structure containing small fibrils and highly apertured areas. It delivers good aesthetics, fabric feel, and efficient fluid transport, is clean and dry in use, is extremely soft, and lint-free.

In a preferred embodiment, the delivery facing has three dimensional containment and wiping functionality. This is most advantageous for a drug product where control of dosage for safety and efficacy are important. Preferably, the delivery facing should contain tube-like holes, which substantially eliminate the previously defined problem of entrapment. By simple finger pressure, the contents are relatively easily dispensed to the part of the body or substrate requiring the drug. Convenience of use together with softness, less messy, excellent control of dosage offer a significant improvement over the prior art. Preferably, the delivery facing is made from "APEX"-type film products, as set forth in U.S. patent application Ser. No. 07/744,744, which is hereby incorporated herein by reference. Preferably the delivery facing is a tricot-type APEX film having from about 5 to about 10% open area. This film is very soft and fabric-like, has maximum active ingredient containment before use and minimum residue entrapment after use. Theoretically, each open area serves as a small tube. The amount of application can be controlled by the pressure applied. As described therein the APEX fabric/film and process render versatility in design and delivery of the product onto hair and skin. Depending upon the nature of the active ingredient and its formulation, the number, size and position of the apertures in the surface of the film may be altered. The three dimensional nature and fibril/space structure allows the product to be easily charged into the fabric. These combined properties offer the user convenience, safety of use, control of dosage, integrity from product spoilage such as ultraviolet light and the like at a cost-effective level. The delivery facing is preferably made of a perforated or reticulated polyethylene or polyethylene/ethylene vinyl acetate film or a light-weight hydrophobic nonwoven fabric made from: polyethylene/polyethylene terephthalate or a polyethylene/polypropylene (bicomponent fiber, such as BICO available from BASF), polyethylene or polypropylene spunbonded, polypropylene fiber. It can also be a RETICULON® film as described in U.S. Pat. Nos. 4,690,679 and 4,710,186, which are hereby incorporated herein by reference.

Apertures in the films of the delivery facing of this invention can have an equivalent circular diameter (ECD) of from about 2 to about 25 mils, more preferably from about 2 to about 7 mils. It can have from about 100 to about 10,000 apertures per square inch. Preferably, it should be from about 5 to about 20 mils in thickness, more preferably from about 10 to about 20 mils, most preferably from about 13 to about 15 mils.

The active ingredient is preferably contained in a viscous gel, cream or ointment formulation in order for maximum drug delivery control. The viscosity of the active ingredient formulation should be from about 10,000 to about 10,000,000 cPs. of course, if the delivery facing has larger apertures, it can accommodate a delivery of a formulation of higher viscosity if the facing has smaller apertures. it can accommodate the delivery of a formulation of very low viscosity such as an oil. Those of ordinary skill in the art can adjust the viscosity of the active ingredient formulation, depending upon the aperture-size of the delivery facing, or vice versa. Components of acceptable gels, creams or ointments are well-known to those of ordinary skill.

Preferably, the pouch products of this invention contain a finger grab on the exterior of the impermeable backing. This finger grab can be an additional facing which is folded and sealed to the impermeable facing on three sides, leaving a fourth area free to accommodate a finger or fingers. This finger grab facilitates wiping and delivery of the dermatological product to the substrate. It also prevents the pouch from slipping and flapping around. The finger grab is preferably a polyolefin film, such as polyethylene, polyethylene/ethylene vinyl acetate coextruded film, or polypropylene/ethylene vinyl acaetate coextruded film.

One embodiment of the novel delivery product of this invention is shown in FIG. 1. Pouch product 10 contains the following elements. Impervious backing 20 is coated with an active ingredient formulation coating 30 in paste or gel form. Adjacent coating 30 is delivery facing 40, having a coating-facing side and an outward-facing side. Delivery facing 40 is sealed to impervious backing 20 around their perimeters. Adjacent the outward-facing side of delivery facing 40 is detachable cover 50, which has a delivery facing side and an outward-facing side. Delivery facing 40 is sealed to detachable cover 50 around their perimeters. The seal strength between delivery facing 40 and detachable cover 50 is weaker than that between delivery facing 40 and impervious backing 20, such that when detachable cover 50 is peeled from delivery facing 40, delivery facing 40 remains affixed to impervious backing 20. Detachable cover 50 has an anterior end 55 and a posterior end 57. At the anterior end 55, detachable cover 50 optionally contains a peel tab 60, which is shorter than the length of the detachable cover from anterior end 55 to posterior end 57. Peel tab 60 is preferably sealed to detachable cover 50 only at the anterior end 55 of the detachable cover 50. The seal strength between peel tab 60 and detachable cover 50 is preferably greater than that between detachable cover 50 and delivery facing 40, so as to permit the peel tab 60 to remove detachable cover 50 from delivery facing 40 without removing detachable cover 50 from impervious backing 20 as well.

Preferably, the products of this invention contain a finger pocket 70 on the outward-facing side of impervious backing 20. Finger pocket 70 is preferably shorter than impervious backing 20 and is preferably sealed to impervious backing 20 around its perimeter, but for one loose portion 75. Finger pocket 70 is preferably large enough to accommodate at least one of the user's fingers.

Figure 2:
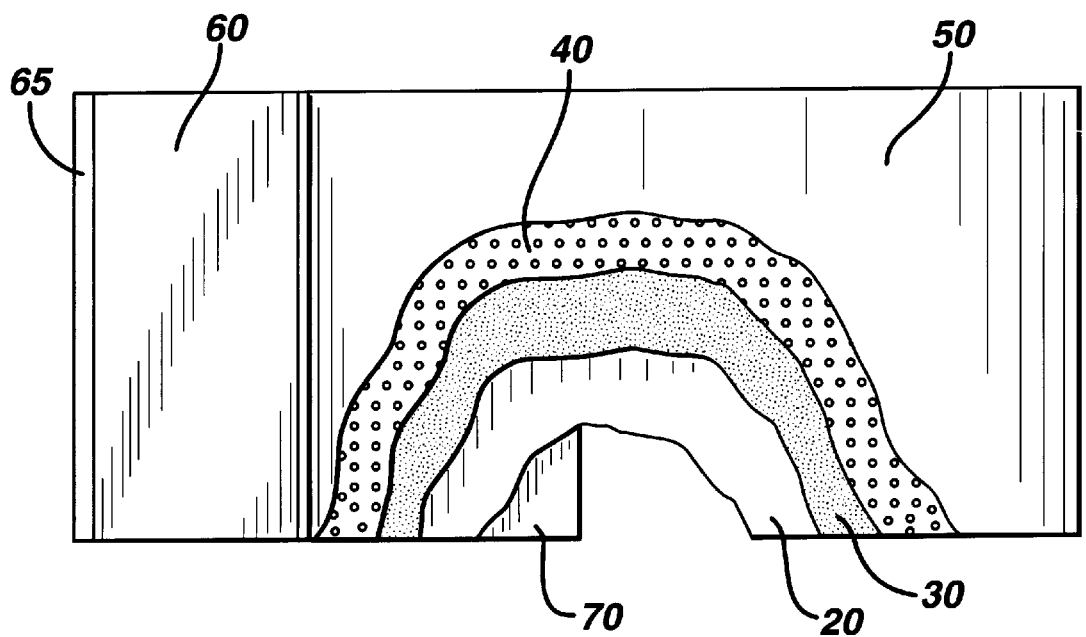
FIG. 2 depicts a cutaway plan view of the top of the pouch of FIG. 1.

FIG. 2 depicts a cutaway view of the top of product 10, wherein peel tab 60 is affixed to detachable cover 50 along line 65. The construction of the product can be seen clearly, as coating 30 is applied to impermeable backing 20. Delivery facing 40 overlies cotaing 30 as well as impermeable backing 20.

Most preferably, the products of this invention contain a peel tab composed of polypropylene coextruded with ethylene vinyl acetate; a detachable cover made from polypropylene, wherein the detachable cover is sealed to the polypropylene side of the peel tab; and the remaining layers made up of polyethylene or a coextruded film of polyethylene and ethylene vinyl acetate. Preferably, delivery facing and impermeable backing are sealed such that the polyethylene sides are sealed together.

Figure 3:
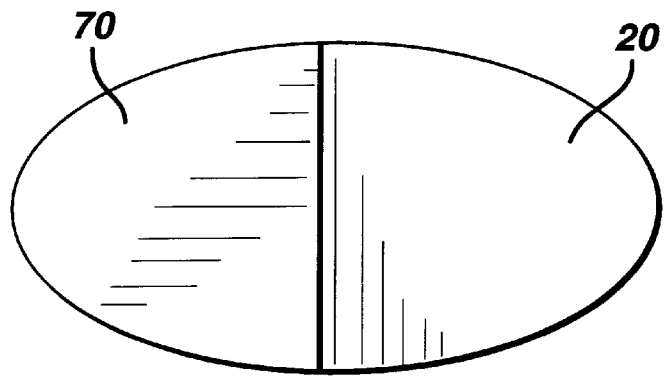
FIG. 3 depicts a plan view of the bottom of a delivery system pouch according to this invention.
Figure 4:
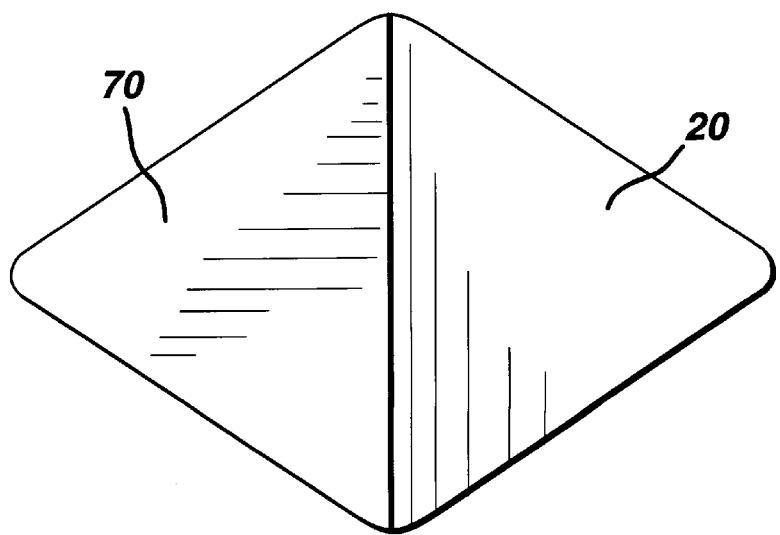
FIG. 4 depicts a plan view of another embodiment of a delivery system pouch according to this inveniton.

As set forth in FIGS. 2, 3 and 4, the pouch products of this invention may be rectangular, square, round or oval in shape or any shape that is within the skill of one of ordinary skill in the art.

The system is particularly advantageous where drug delivery to abraded skin such as diaper rash, wounds or the like represents a potential problem with cross-infection, particularly from HIV virus or the like. It can be designed for multiple use and/or one-use and is disposable, as the system is environmentally acceptable.

Active ingredients which can be dispensed using the products of this invention include, but are not limited to: antimicrobials, deodorants, antiperspirants, skin and hair care products, retinoids, vaginal products, facial acne products, rectal cleansers, anti-itch powders, diaper rash, hair and body cleansers, conditioners, wound cleansers, and any others known to those of ordinary skill in the art.

The products of this invention are particularly well-suited for the application of antifungal products to the skin. This format is particularly attractive because the therapeutic agent is aliquotted, and neatly packaged to minimize finger contact with the lesion as well as with the agent. In practice, fungal/yeast infections are often found in moist intertriginous regions, such the inguinal, under-breast, and axillary areas, as well as the foot. Many patients find treating these areas with a bare finger offensive and would prefer using an inert support. The pouch format is particularly attractive since the drug used is already aliquotted and the patient has an immediate, contained and clean tool for application. For example, an antimycotic such as Spectazole cream (1% econazole nitrate) is particularly well-suited for this type of application.

The following examples illustrate the embodiment of the invention, however, they do not limit its use within the entire spirit and scope.

EXAMPLES 1, 2 AND 3 MAKING THE DELIVERY FACING

A perforation line for making APEX film is equipped with a driven unwind, a drum with a forming surface, three manifolds, a drying section, and a winder. The manifolds provide constrained liquid steam as an energy source. The forming surface contains a plurality of openings extending through the thickness of the drum.

There are two sizes of openings staggered in rows (the rows being oriented in the cross-direction) along the machine direction. The space between sets of one row of larger openings and one row of smaller openings is greater than the space between one row of larger and one row of smaller openings within the set. The top portion of each opening has a conical shape. The conical shaped surfaces are relatively smooth with varying undulations.

EXAMPLE 1

A film material was made using Exxon Chemical EMB-631 polyethylene, having a thickness of 0.8 mil. The material was run at a rate of 50 yards per minute (ypm). The manifolds were held at a pressure of 1350 pounds per square inch (psi). The water temperature was 160° F. water. The resulting film had an open area of about 10%, an average hole size of ECD 5 mil and a hole size ECD variation coefficient of 58%. The Frazier air value of the film was 350 cfm.

EXAMPLE 2

A film material was made using Exxon Chemical EMB-631 polyethylene, having a thickness of 0.80 mil. The material was run at a rate of 50 yards per minute (ypm). The manifolds were held at a pressure of 1000 pounds per square inch (psi). The water temperature was 160° F. water. The resulting film had an open area of about 3%, an average hole size of ECD 3 mil and a hole size ECD variation coefficient of 54%. The Prazier air value of the film was 200 cfm. The film contained approximately 3,400 holes per square inch.

EXAMPLE 3

A film material was made using Exxon Chemical EMB-631 polyethylene, having a thickness of 0.95 mil. The material was run at 50 yards per minute (YPM). The manifolds were held at a pressure of 1350 pounds per square inch (psi). The water temperture was 160F. The resulting film had an open area of about 5%, an average hole size of ECD 3 mil and a holes ECD variation coefficient of 73%.

The Frazier air value of the film was 288 cfm. The film contained approximately 4,790 holes per square inch.

EXAMPLE 4

An employee lab usage study of a disposable diaper rash ointment pouch was performed. The objective of the study was to evaluate acceptability of a ready to use disposable pouch containing a layer of diaper rash ointment.

Thirty pouches containing a target weight of 3 grams of diaper rash ointment for an in-use test were produced.

The pouches had four layers constructed as follows: The bottom sheet was made of Exxon polyethylene film EMB-633, having a thickness of 1.25 mil. Over this layer was applied zinc oxide ointment in the amount of 2 grams (g). Apex tricot film made in accordance with the process set forth in Example 2, made of EMB-631 polyethylene film, having a thickness of 13 mil, an open area of 3%, a hole size of 3 mils was then applied over the zinc oxide ointment to the backing film of polyethylene, sleeve side up. The ointment was coated onto the backsheet with a coater knife (Pacific Scientific) set at 1 full turn pass zero and at 22.0. The ointment was coated over a window cut into a MYLAR (available from E. I. duPont de Nemours of Wilmington, Delaware) thermoplastic material. A detachable facing layer composed of Exxon EMB-631 polyethylene film having a thickness of about 0.8 mil was then applied to the delivery facing layer using heat. The materials were assembled and placed onto a Jenkins press, heat-sealed and die cut using 80 psi air pressure, 265° F. temperature. The seal strength between the delivery facing and the impervious backing sheet was greater than that between the delivery facing and the detachable cover due to the difference in the material used in the product.

EXAMPLE 5

The products made in accordance with Example 3 were tested by use on human subjects, by removing the detachable cover and applying the zinc oxide ointment using a wiping motion to either of the subjects' arms. Participants in the study then were asked the following questions, to which they responded as set forth below.

Question 1: How much better this dispensing method was over the current method?

| | |
|---|---|
| Better: | 21/36 (58%) |
| Much Better: | 15/42% |
| Somewhat Better: | 3/8% |
| Slightly Better: | 3/8% |
| No Better/No Worse: | 1/36 (3%) |
| Worse: | 14/36 (39%) |
| | 9/25% Pouch Related |
| | 5/14% Ointment Related |

EXAMPLE 6—WOUND/SKIN CLEANSER AND ANTISEPTIC

An antimicrobial product containing 2% chlorohexadine gluconate, amine oxide, fragrance, thickener and fragrance are prepared and incorporated into a pouch product in accordance with Example 4. are prepared in the same manner.

EXAMPLE 7—BODY POWDER

Talc and fragrance were incorporated into the pouch in accordance with the method set forth in Example 4. The pouch application of talc and fragrance in accordance with the teachings of this invention produced less dust or fines upon use compared to conventional packaging.

EXAMPLE 8—HAIR/BODY CLEANSER

A standard gel shampoo system of 20% sodium lauryl (3) ether sulfate, 3% lauric diethanolamide, thickener, preservative dyes and fragrance in a water base are prepared. The gel shampoo system is incorporated into a pouch product in accordance with the method set forth in Example 4. The product dispenses easily and foams copiously on hair and/or skin.

EXAMPLE 9—VAGINAL LUBRICANT/SPERMICIDE

A vaginal lubricant such as K-Y* Jelly is incorporated into the products of this invention in accordance with Example 4. The pouch products of this invention can be readily inserted and wiped across the vagina in order to dispense vaginal lubricant and/or a spermicide formulation internally without occasioning excess material on the fingers.

EXAMPLE 10—SPECTAZOLE CREAM

It was the purpose of this study to test the efficacy of Spectazole cream (1% econazole nitrate) in a pouch format versus a conventional format for the treatment of a dermatophytic infection in the guinea pig.

*Trichophyton mentagrophytes* (#9201) was grown on Sabouraud's dextrose agar (SDA) in Roux bottles for 14–15 days at 32 C. Fungal spores were removed with a small volume of Tween-saline and the suspension was poured into a graduated cylinder. The mixture was diluted 1:1 with honey and homogenized in a blender. The suspension was then filtered through a funnel lined with a sterile gauze pad.

Female Harley guinea pigs, 350–450 g, were obtained from Charles River Laboratories. Each animal was weighed and the anesthetized with an injection of Nembutal (30 mg/kg). An app 6 cm square region on the dorsal surface of the animal was shaved and abraded. One ml of the culture suspension was applied to the dorsal skin of the animal to initiate infection. Beginning three days after infection, animals were treated topically with Spectazole cream (1% econazole nitrate) once daily (animals were not treated on Sundays) for a total of fourteen days. The Spectazole was applied either with a wooden applicator or a pouch made in accordance with this invention as described in Example 3 above. As a control one group of infected animals was left untreated.

Three days after infection, at least five hairs from five separate regions in the infected area were plucked and placed onto Dermatophyte test medium (DTM). Cultures were incubated for two weeks at 32 C., after which the culture vials were examined for the presence of the organism by fungal culturing. Characteristic fungal growth (i.e., a positive culture) turns the culture medium pink, whereas, no growth (i.e., a negative culture) leaves the medium orange. Animals were cultured for *Trichophyton mentagrophytes* at weekly intervals including one week after the final treatment. For the experiment, the infected lesions of three animal groups, each made of ten guinea pigs, were studied: one group was left untreated, one group was treated daily with one gram of Spectazole cream on a wooden applicator, and the final group was treated daily with the pouch of this invention. The pouch contained two grams of total reagent; preliminary experiments demonstrated that 50% of the total reagent was expressed from the pouch by vigorous wiping.

Figure 5:
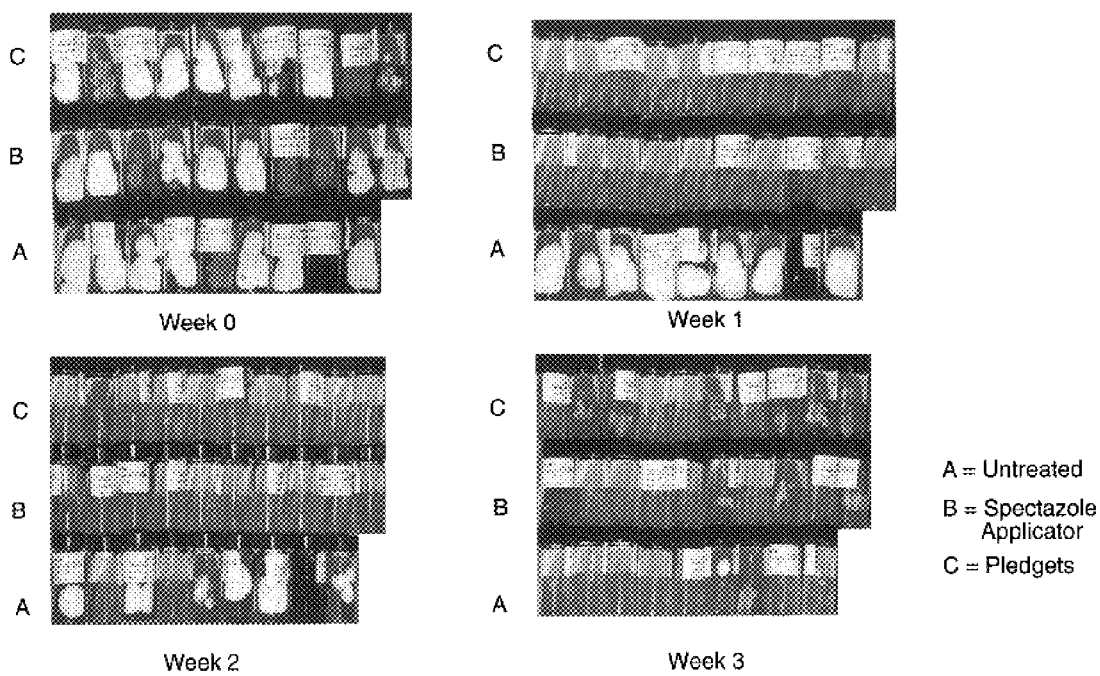
FIG. 5 depicts culture tubes inoculated with samples taken from female Harley Guinea Pigs as set forth in Example 10 below.

Results are set forth in Table 1 below and in FIG. 5. It can be seen from examining the Table and Figures that at the initiation of the experiment, at least seven of the animals in each group cultured positive for fungi. After one week of treatment, eight of the untreated animals cultured positive but none of the treated animals. At the end of two weeks, six of the untreated animals continued to demonstrate viable fungus but the two treated groups were again negative. At the end of three weeks, the data show that the infection burned itself out (a characteristic of this animal), but it is significant that infection did not reappear in the treated groups. Thus, the application of an antimycotic using the pouch products of this invention is at least as effective as the conventional applicator method and demonstrates that it is effective as a method of delivery antifungal agents.

TABLE I

Presence of fungal growth (*T. mentagrophytes*) after Infection*

| ANIMAL # | WEEK 0 Plucked 1/6 Read 1/20 | WEEK 1 Plucked 1/13 Read 1/27 | WEEK 2 Plucked 1/20 Read 2/3 | WEEK 3 Plucked 1/27 Read 2/10 |
|---|---|---|---|---|
| UNTREATED | | | | |
| 1 | + | + | + | − |
| 2 | + | + | − | − |
| 3 | + | + | + | − |
| 4 | + | + | − | − |
| 5 | − | + | + | − |
| 6 | + | + | + | + |
| 7 | + | + | + | − |
| 8 | − | − | − | − |
| 9 | + | + | + | − |
| TOPICAL | | | | |
| 10 | + | − | − | − |
| 11 | + | − | − | − |
| 12 | − | − | − | − |
| 13 | + | − | − | − |
| 14 | + | − | − | − |
| 15 | + | − | − | − |
| 16 | − | − | − | − |
| 17 | − | − | − | − |
| 18 | + | − | − | − |
| 19 | + | − | − | − |
| PLEDGETS | | | | |
| 20 | + | − | − | − |
| 21 | − | − | − | − |
| 22 | + | − | − | − |
| 23 | + | − | − | − |
| 24 | + | − | − | − |
| 25 | + | − | − | − |
| 26 | + | − | − | − |
| 27 | + | − | − | − |
| 28 | − | − | − | − |
| 29 | + | − | − | − |

*+, culture positive
−, culture negative

What is claimed is:

1. A wipable topical formulation delivery system comprising:
   (a) a fluid-impermeable backing sheet, said backing sheet having an interior side and an exterior side;
   (b) a dispensable coating of topical formulation deposited on said fluid-impermeable backing sheet on its interior side; and
   (c) a delivery facing with a three-dimensional structure which contains apertures that serve as small tubes of sufficient diameter and thickness to permit delivery of a controlled dose of said topical formulation without entrapment of said formulation in the facing, and having a coating-facing side and an exterior side, superimposed over said coating of said topical formulation and affixed to the interior side of said fluid-impermeable backing sheet said controlled dose of said dispensable coating being dispensed upon pressure exerted thereupon.

2. A topical formulation delivery system according to claim 1 which further comprises:
   (d) a detachable cover adjacent said delivery facing on exterior side of said delivery facing and releasably affixed thereto, said detachable cover having a side facing said delivery facing and an exterior side, the peel strength of said affixation between the detachable cover and the delivery facing being weaker than the peel strength of the affixation between said delivery facing and said impermeable backing.

3. A topical formulation delivery system according to claim 2 which further comprises:

(e) a peel tab adjacent to said detachable cover on its exterior side and affixed thereto, said peel tab being adaptable to removing said detachable cover from said delivery facing upon being subjected to a pulling force, the peel strength of the affixation between said peel tab and said detachable cover being greater than the peel strength of the affixation between said detachable cover and said delivery facing.

4. A topical formulation delivery system according to claim 3 which further comprises:

(f) a finger pocket affixed to the exterior side of said impermeable backing, the finger pocket comprising a sheet of material affixed such that one edge is free from affixation in order to accommodate a finger.

5. A topical formulation delivery system according to claim 1 wherein said impermeable backing comprises a polymer film.

6. A topical formulation delivery system according to claim 5 wherein said polymer film comprises a polyolefin.

7. A topical formulation delivery system according to claim 6 wherein said polymer film material is polyethylene or polyethylene/ethylene vinyl acetate coextruded film.

8. A topical formulation delivery system according to claim 1 wherein said delivery facing comprises an apertured polymer film.

9. A topical formulation delivery system according to claim 8 wherein said delivery facing comprises an apertured polymer film having from about 100 to about 10,000 apertures per square inch.

10. A topical formulation delivery system according to claim 9 wherein said apertures have an equivalent circular diameter of from about 2 to about 25 mils.

11. A topical formulation delivery system according to claim 2 wherein the peel strength of the affixation between the delivery facing and the detachable cover is weaker than that between the detachable cover and the impermeable backing.

12. A topical formulation delivery system according to claim 2 wherein the peel force of the affixation between the delivery facing and the detachable cover is from about 1 to about 4 pounds.

13. A topical formulation delivery system according to claim 6 wherein said polyolefin is selected from the group consisting of: polyethylene, polypropylene, or polyethylene coextruded with ethylene vinyl acetate, or polypropylene coextruded with ethylene vinyl acetate.

14. A topical formulation delivery system according to claim 8 wherein said delivery facing has a thickness of from about 5 to about 20.

15. A topical formulation delivery system according to claim 10 wherein said ECD is from about 2 to about 7 mils.

16. A topical formulation delivery system according to claim 10 wherein said thickness is from about 13 to 15 mils.

* * * * *